United States Patent [19]

Litterer et al.

[11] Patent Number: 4,605,809
[45] Date of Patent: Aug. 12, 1986

[54] ALUMINOSILICATES AND SILICA GELS HAVING A LOW CONTENT OF TRANSITION ELEMENTS, A PROCESS FOR THEIR USE IN THE CONVERSION OF METHANOL TO OLEFINS

[75] Inventors: Heinz Litterer, Wiesbaden; Friedrich Wunder, Flörsheim am Main; Ernst I. Leupold, Neu-Anspach; Herbert Baltes, Frankfurt am Main, all of Fed. Rep. of Germany

[73] Assignee: Hoechst Aktiengesellschaft, Frankfurt am Main, Fed. Rep. of Germany

[21] Appl. No.: 545,957

[22] Filed: Oct. 27, 1983

Related U.S. Application Data

[62] Division of Ser. No. 410,910, Aug. 24, 1982, abandoned.

[30] Foreign Application Priority Data

Aug. 26, 1981 [DE] Fed. Rep. of Germany ....... 3133747

[51] Int. Cl.$^4$ .............................................. C07C 1/24
[52] U.S. Cl. .................................. 585/640; 423/328; 502/520
[58] Field of Search ............... 585/640, 639; 423/328; 502/520

[56] References Cited

U.S. PATENT DOCUMENTS

| | | | |
|---|---|---|---|
| 1,913,938 | 6/1933 | Metzger et al. | 585/640 |
| 3,803,046 | 4/1974 | Winyall et al. | 423/338 |
| 4,052,479 | 10/1977 | Chang et al. | 585/640 |
| 4,207,424 | 6/1980 | Winnick | 585/640 |
| 4,260,841 | 4/1981 | Holland et al. | 585/640 |
| 4,260,845 | 4/1981 | Shioyama | 585/640 |
| 4,278,565 | 7/1981 | Chen et al. | 585/640 |
| 4,296,266 | 10/1981 | Wunder et al. | 585/640 |
| 4,398,050 | 8/1983 | Hofstadt et al. | 585/640 |
| 4,423,270 | 12/1983 | Pearson | 585/639 |
| 4,423,273 | 12/1983 | Hoelderich et al. | 585/640 |
| 4,433,189 | 2/1984 | Young | 585/640 |
| 4,447,669 | 5/1984 | Hamon et al. | 585/639 |
| 4,471,150 | 9/1984 | Wu | 585/640 |
| 4,481,376 | 11/1984 | Wunder et al. | 585/640 |

FOREIGN PATENT DOCUMENTS

| 0457938 | 7/1949 | Canada | 585/640 |
|---|---|---|---|
| 1061847 | 3/1967 | United Kingdom | 423/328 |

OTHER PUBLICATIONS

Fredrich Wunder et al., "Lower Olefins from Methanol-Water Mixtures", Chem. Abstract, 94:191655R.
Chem. Abstracts, vol. 87, Nov., 1977, p. 115, No. 169961w.
Zeolite Technology and Applications, Chemical Technology Review No. 170, published by Noyes Data Corporation 19-0, p. 207, Example 1.

*Primary Examiner*—Andrew H. Metz
*Assistant Examiner*—Anthony McFarlane
*Attorney, Agent, or Firm*—Curtis, Morris & Safford

[57] ABSTRACT

The present invention relates to aluminosilicates and silica gels having a low content of transition elements, to a process for their manufacture and to their use as a catalysts or catalyst supports. Said aluminosilicates or silica gels are prepared by treating them with a solution of complexing agents at a temperature of from 70° to 150° C. The manufacture of low-molecular-weight olefins from methanol is one possible application field of said aluminosilicates, used as a catalyst.

6 Claims, No Drawings

ALUMINOSILICATES AND SILICA GELS HAVING A LOW CONTENT OF TRANSITION ELEMENTS, A PROCESS FOR THEIR USE IN THE CONVERSION OF METHANOL TO OLEFINS

This is a division of application Ser. No. 410,910 filed Aug. 24, 1982, now abandoned.

The present invention relates to aluminosilicates and silica gels having a low content of transition elements, to a process for their manufacture and to their use as catalysts as catalyst carriers.

The transition elements in question are, in particular, Cu, Ni, V, Ti, Zr, Co and more particularly Fe. They may be present as metals or as compounds.

It is known from literature that transition elements, in particular iron, have a troublesome influence on a great number of reactions involving heterogeneous catalysts, especially because they reduce the selectivity (Furimski, E., Erdöl und Kohle (1979), 32, (8), 383).

Natural zeolites frequently contain transition elements. Other aluminosilicates and silica gels are frequently contaminated with transition elements during their manufacture.

Purification processes using dilute mineral acids are known for removing transition elements from silica gels and acid-resistant aluminosilicates.

Frequently, however, these processes result in a disadvantageous acidity and they are not very effective. They are totally unsuitable for acid-sensitive aluminosilicates.

An economic process for removing transition elements from zeolites or other aluminosilicates using complexing agents without changing the aluminum content has not been known hitherto. German Offenlegungsschrift No. 2,928,922 discloses a process for preparing $C_2$–$C_4$ olefins from methanol and/or dimethyl ether in the presence of water and in the presence of a manganese-containing aluminosilicate catalyst, which comprises washing out the catalyst with a solution of ethylene diamine tetraacetic acid or tartaric acid at a pH of from 3 to 7. The temperature of the solution is preferably between 0° to 50° C. Manganese may be applied to the carrier prior to or after this washing step. It follows that the transition element manganese is not removed during this washing step, and said removal is not at all intended. On the contrary, these measures aim at providing a manganese-containing catalyst for the manufacture of olefins from methanol and/or dimethyl ether which is stable to considerable quantities of water.

Subject of the present invention therefore are aluminosilicates or silica gels having a low content of transition elements, characterized in that the aluminosilicates or silica gels have been treated with solutions of complexing agents at a temperature of from 70° to 150° C.

Subject of the present invention furthermore is a process for the manufacture of aluminosilicates or silica gels having a low content of transition elements, which comprises treating the aluminosilicates or silica gels with solutions of complexing agents, at a temperature of from 70° to 150° C. As a result, the transition elements are removed nearly quantitatively. This applies in particular to the most frequent contaminant, namely iron. Operation is carried out preferably at a temperature of from 80° to 120° C., in particular of from 90° to 110° C.

Subject of the present invention finally is the use of the above-treated aluminosilicates or silica gels as catalysts or catalyst supports in reaction steps of organic compounds, which comprises contacting the compounds with said aluminosilicates or silica gels, under the reaction conditions applied, optionally after addition of a catalytically active substance.

The time of treatment with the solutions of complexing agents is generally from 10 to 150 hours, preferably from 40 to 120 hours. The time of treatment may be substantially longer in the case of particularly stable types of zeolites such as mordenite or ferrierite, but this is not required, however.

The fact that synthetic and natural zeolites as well as other aluminosilicates contaminated with transition elements can be purified in nearly quantitative manner according to the invention within an economically acceptable period of time, without removal of excessive portions of the skeleton aluminum, is extremely surprising. Even natural small-pored zeolites having pore openings of less than 4.5 Å are freed nearly quantitatively from iron contaminants when using complexing agents, the kinetic molecular diameter of which is substantially greater than 4.5 Å. When removing iron or other transition elements from silica gel in the manner according to the invention the results are better than when using dilute mineral acids.

Suitable complexing agents are chelate-forming carboxylic acids, such as hydroxycarboxylic acids (in particular tartaric acid and citric acid) or aminocarboxylic acids (in particular ethylene diamine tetraacetic acid, hydroxyethylene diamine tetraacetic acid and nitrilotriacetic acid). Further suitable compounds include 1,3-diketones (in particular acetyl acetone and trifluoroacetyl acetone), amino alcohols, amino phenols, phosphoric acids, phosphonic acids (in particular ethylene diamine tetramethylene phosphonic acid and nitrilotrimethylene phosphonic acid). Derivatives of said compounds are also suitable. Inorganic cyanides and rhodamides may likewise be used. Preference is given to chelate-forming carboxylic acids, phosphoric acids or phosphoric acids or derivatives thereof. Particularly suitable are salts of ethylene diamine tetraacetic acid and of ethylene diamine tetramethylene phosphonic acid.

When proceeding according to the present invention, transition elements such as Cu, Ni, V, Ti, Zr, Co and in particularly Fe are removed practically completely.

Suitable solvents are water, organic solvents such as methanol or formamide, mixtures of organic solvents or water-containing organic solvents or solvent mixtures. Preference is given to water, water-containing organic solvents or water-containing organic solvent mixtures. High-boiling alcohols or carboxylic acids may be used alternatively in particular at relatively high reaction temperatures.

The process according to the invention is carried out generally under atmospheric pressure or under the corresponding vapor pressure of the solvent. It is possible, however, to adjust the pressure to special requirements by addition of inert gases.

The organic complexing agent is generally used at a concentration of from 3 to 40 weight %, referred to the respective solvent, preferably of from 7 to 30 weight %.

The process may be carried out in continuous manner as well as in discontinuous manner in the usual reaction vessels.

The volume ratio of the solution of complexing agent to aluminosilicate and silica gel, respectively, is generally from 0.3 to 10.

After removal of the solvent and complexing agent, the aluminosilicates or silica gels, freed from transition elements according to the invention, may be used as catalysts or catalyst supports.

The following application fields should be mentioned in particular: The conversion of methanol to short chain olefins in the presence of small-pored natural zeolites, the selective cracking (selectoforming) in the presence of natural zeolites of the types erionite and ferrierite as well as the selective alkylation of benzene and derivatives thereof in the presence of natural ferrierite catalysts.

The present invention is illustrated in greater detail in the following examples, without being limited by them. The tests are conducted in externally heated continuously operated agitator vessels.

EXAMPLE 1

200 g of a natural chabazite-erionite mixture having an iron content of 2.6 weight % is reacted with 800 g of a 10 weight % aqueous solution of ethylene diamine tetraacetic acid for 96 hours at 140° C. Upon completion of the reaction, the iron content is below 0.2 weight %. The silicon-aluminum ratio of this zeolite mixture has increased to a small extent from 3.90 to 4.04.

EXAMPLE 2

To 100 g of a natural chabazine-erionite mixture having an iron content of 1.8 weight % there are added 1,000 g of a 5 weight % aqueous solution of the disodium salt of ethylene diamine tetraacetic acid and the batch is heated at 70° C. for 120 hours, while stirring.

Upon completion of the reaction, the silicon-aluminum ratio has increased from 4.0 to 4.15. The iron content of the zeolite mixture is only as little as 0.3 weight %.

EXAMPLE 3

100 g of a natural chabazite having a Si/Al ratio of 3.03 and an iron content of 2.8 weight % are reacted with 1,000 g of a 20 weight % aqueous solution of the sodium salt of ethylene diamine tetraacetic acid for 48 hours under reflux conditions.

The iron content of the zeolite is only as little as 0.3 weight %. The silicon-aluminum ratio has increased from 3.03 to 3.30.

EXAMPLE 4

100 g of an iron-containing natural ferrierite are reacted with 1,000 ml of a 10 weight % aqueous solution of the Na-salt of ethylene diamine tetramethylene phosphonic acid for 72 hours under reflux conditions. Upon completion of the reaction, the iron content of the aluminosilicate has dropped from 2.4 to 0.2%.

The silicon-aluminum ratio has increased from 4.95 to 5.05.

EXAMPLE 5

This example serves to demonstrate the selectivity-improving action of the process according to the invention on a zeolite catalyst used in the conversion of methanol to low-molecular weight olefins. 520 ml of 50 weight % aqueous methanol per hour are fed to a vertically arranged electrically heated tube reactor of 1 m length, which is charged with 250 ml of catalyst, at a temperature of 400° C. The reaction mixture is allowed to cool, the condensable portions are separated and the gaseous phase is analyzed. This test is carried out using the catalyst treating according to the invention and an untreated zeolite catalyst:

(a) When using a chabazite-erionite mixture treated according to the process of the present invention, in which the iron content has been reduced to 0.2 weight %, a selectivity of $C_2$–$C_4$ olefins of 83% was obtained.

(b) When using an untreated chabazite-erionite mixture having an iron content of 2.9 weight %, a selectivity of $C_2$–$C_4$ olefins of 61% was obtained.

What is claimed is:

1. A method for preparing a $C_2$–$C_4$ olefin from methanol which comprises contacting methanol, with an aluminosilicate or silica gel which contains a transition element, said aluminosilicate or silica gel having been prepared by treating said aluminosilicate or silica gel with a solution of a complexing agent at a temperature of 70° to 150° C. to wherein the content of the transition element is reduced in an amount of from at least 1.8 percent by weight to 0.5 percent by weight or less whereby the selectivity of the $C_2$–$C_4$ olefin is improved.

2. The method, as claimed in claim 1, wherein the complexing agent is a chelate-forming carboxylic acid, a phosphoric acid, a phosphonic acid or a derivative thereof.

3. The method, as claimed in claim 1, wherein the complexing agent is in solution in water or a water-containing organic solvent.

4. The method, as claimed in claim in 1, wherein the aluminosilicate or silica gel is treated for 10 to 150 hours.

5. The method, as claimed in claim 1, wherein the transition element is iron.

6. The method, as claimed in claim 1, wherein the transition element is copper, nickel, vanadium, titanium, zirconium, iron or cobalt.

* * * * *

UNITED STATES PATENT AND TRADEMARK OFFICE
CERTIFICATE OF CORRECTION

PATENT NO. : 4,605,809

DATED : August 12, 1986

INVENTOR(S) : Litterer et al.

It is certified that error appears in the above-identified patent and that said Letters Patent is hereby corrected as shown below:

Column 4, line 36 (Claim 1, line 9), change "0.5" to --0.3--;

Column 4, line 40 (Claim 2, line 3), delete "a", all three occurrences.

Signed and Sealed this

Eighth Day of September, 1987

Attest:

DONALD J. QUIGG

Attesting Officer   Commissioner of Patents and Trademarks